(12) United States Patent
Daitho

(10) Patent No.: US 7,862,997 B2
(45) Date of Patent: Jan. 4, 2011

(54) PRIMER AND PRIMER SET FOR AMPLIFICATION OF CEA NUCLEIC ACID, AND METHOD FOR ASSISTING CANCER DIAGNOSIS

(75) Inventor: Motonari Daitho, Hamburg (DE)

(73) Assignee: Sysmex Corporation, Kobe (JP)

( * ) Notice: Subject to any disclaimer, the term of this patent is extended or adjusted under 35 U.S.C. 154(b) by 732 days.

(21) Appl. No.: 11/698,169

(22) Filed: Jan. 26, 2007

(65) Prior Publication Data

US 2007/0190563 A1   Aug. 16, 2007

(30) Foreign Application Priority Data

Jan. 27, 2006   (JP) .............................. 2006-019673

(51) Int. Cl.
*C12Q 1/68* (2006.01)
*C12P 19/34* (2006.01)
*C07H 21/04* (2006.01)

(52) U.S. Cl. ........................ 435/6; 435/91.2; 536/24.33

(58) Field of Classification Search ........................ None
See application file for complete search history.

(56) References Cited

U.S. PATENT DOCUMENTS

2004/0175729 A1   9/2004   Hiyama

FOREIGN PATENT DOCUMENTS

| EP | 1 020 534 A1 | 7/2000 |
|---|---|---|
| WO | WO 02/070751 A1 | 9/2002 |
| WO | WO 2004/099247 A2 | 11/2004 |
| WO | WO 2004099247 A2 * | 11/2004 |

OTHER PUBLICATIONS

Notomi et al. (2000) Nucleic acid research vol. 28 No. 12 e63 pp. i-vii.*

Database EMBL [Online], Sep. 4, 2002, "*IL-6 receptor derivative*", retrieved from EBI accession No. EMBL: BD078718, Database accession No. BD078718, XP002435539.

Database EMBL [Online], Jan. 15, 2001,"*PM1-CN0104-281200-001-e05 CN0104 Homosapiens cDNA, mRNA sequence*", retrieved from EBI accession No. EMBL: BF768263, Database accession No. BF768263, XP002435540.

* cited by examiner

*Primary Examiner*—Kenneth R. Horlick
(74) *Attorney, Agent, or Firm*—Sughrue Mion, PLLC

(57) ABSTRACT

The present invention provides a nucleic acid amplification primer which can detect CEA mRNA. Also provided are nucleic acid amplification primer sets, methods to amplify nucleic acid for detecting mRNA of the gene that encodes CEA, and a method for assisting cancer diagnosis.

6 Claims, 3 Drawing Sheets

PRIMER AND PRIMER SET FOR AMPLIFICATION OF CEA NUCLEIC ACID, AND METHOD FOR ASSISTING CANCER DIAGNOSIS

BACKGROUND OF THE INVENTION

1. Field of the Invention

The present invention relates to a nucleic acid amplification primer which is used for nucleic acid amplification of carcinoembryonic antigens, a nucleic acid amplification primer set, and methods for assisting cancer diagnosis.

2. Description of the Related Art

Carcinoembryonic antigen (hereinafter referred to as CEA) is a glycoprotein discovered as an antigen substance which is commonly present in colonic cancer and children's colonic mucosa and one of the most-used tumor marker in recent years. CEA is expressed in various types of cancers such as rectal cancer, colonic cancer, gastric cancer, esophagus cancer, lung cancer, mammary cancer, liver cancer, biliary tract cancer, pancreas cancer, thyroid cancer, bladder cancer, prostate cancer, scrotal cancer, cervix cancer, cancer of uterine body, cervical cancer, and ovarian cancer. Detecting expression of CEA as a tumor marker can provide an indication of cancer diagnosis and followup after operation or treatment such as chemotherapy. Usefulness thereof has been recognized. A method of specifically detecting the expression of CEA, i.e. a tumor marker, is a method (genetic screening) for detecting mRNA of CEA gene (hereinafter referred to as CEAmRNA).

As a primer set for detecting CEAmRNA by genetic screening, a primer set described in US20040175729 is known. The primer set which may be used for the LAMP method or the RT-LAMP method includes two kinds of inner primers (FIP and RIP), two kinds of outer primers (F3P and R3P), and two kinds of loop primers (LPF and LPR).

The above-mentioned primer and primer set can specifically detect CEAmRNA, however the reproducibility of detection is not described in US20040175729.

SUMMARY OF THE INVENTION

The scope of the present invention is defined solely by the appended claims, and is not affected to any degree by the statements within this summary.

The present invention provide a nucleic acid amplification primer, which is used in the nucleic acid amplification method for detecting mRNA of the gene that encodes CEA including: a first base sequence being capable of hybridizing to a first target region or a second target region at the 3' end, and a second base sequence being capable of hybridizing to an elongated strand from the first base sequence at the 5 ' end, wherein the first target region consists of the 704th to 1237th base sequences of SEQ ID NO: 1, and the second target region consists of a complementary base sequence for the first target region.

The present invention further provides a nucleic acid amplification primer set which is used in the nucleic acid amplification method for detecting mRNA of the gene that encodes CEA, the primer set including: a first primer containing a first base sequence being capable of hybridizing to a first target region at the 3' end and a second base sequence being capable of hybridizing to an elongated strand from the first base sequence at the 5' end; a second primer containing a third base sequence being capable of hybridizing to a region further downstream from the region in which the second base sequence is capable of hybridizing in the elongated strand from the first base sequence at the 3' end, and a fourth base sequence being capable of hybridizing in an elongated strand from the third base sequence at the 5' end; and a third primer being capable of hybridizing to a region further downstream from the region in which the third base sequence is capable of hybridizing in the elongated strand from the first base sequence, wherein the first target region consists of the 704th to 1237th base sequences of SEQ ID NO: 1.

Furthermore, the invention provides a method for assisting cancer diagnosis, including the steps of preparing reaction solutions by mixing biological samples collected from individuals, an enzyme having reverse transcription activity, dNTPs, strand displacement DNA polymerase, and the above-mentioned primer set; heating the above-mentioned reaction solution so as to allow the amplification reaction based on mRNA of CEA using the above-mentioned primer set; and measuring the above-mentioned amplification and determining whether mRNA of CEA is present in the biological samples on the basis of measurement.

Furthermore, the invention provides a reagent kit for detecting mRNA of CEA comprising an above mentioned nucleic acid amplification primer, an enzyme having reverse transcription activity, dNTPs, and strand displacement DNA polymerase.

The invention provides a primer with which more reproducible results of detection of CEAmRNA can be obtained than with the conventional nucleic acid amplification primer for detecting CEA. Further, information for assisting cancer diagnosis is also provided by detecting CEAmRNA contained in biological samples using the primer of the invention.

DETAILED DESCRIPTION OF THE EMBODIMENT

Figure 1:
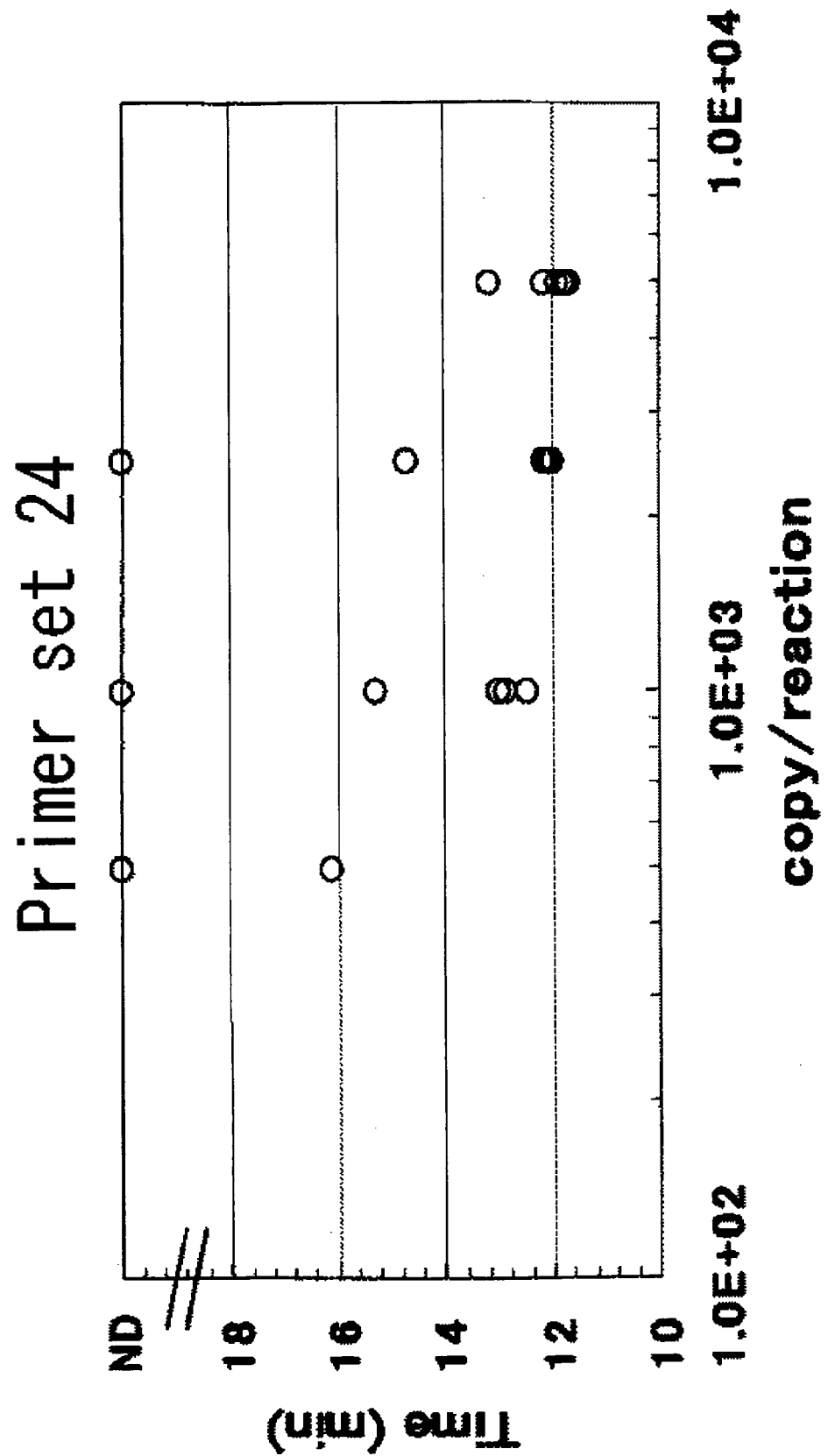
FIG. 1 is a view showing the measurement results of primer set 24 in Example 2.

In an embodiment of the present invention, a primer can be used for the nucleic acid amplification method for detecting CEAmRNA. A base sequence corresponding to a region which can be translated into the amino acid sequence of CEAmRNA, namely Cording sequence (CDS) is described in SEQ ID NO: 1. With reference to SEQ ID NO: 1, uracil (U) contained in the base sequence of RNA is replaced with thymine (T). Examples of nucleic acid amplification method include the polymerase chain reaction (PCR) method, the reverse transcriptase-polymerase chain reaction (RT-PCR) method, the loop-mediated isothermal amplification (LAMP) method, the reverse transcription-loop-mediated isothermal amplification (RT-LAMP) method, but are not limited thereto.

The RT-LAMP method is a nucleic acid amplifying method in which DNA having loop structures at both ends is synthesized by using a target region (RNA) as a template, and then the obtained DNA is used as a starting point of synthesis to amplify DNA. In the embodiment of the present invention, the RT-LAMP method can be used, because of use of CEAmRNA as a template.

A method of designing a primer used for the RT-LAMP method in the embodiment is described in US20040175729. Specifically, primers are designed so as to consist of F3, F2, F1, R1, and R2 regions in this order at the 5' end of CEAm-RNA. F3c denotes a region complementary to F3 region, F2c denotes a region complementary to F2 region, F1c denotes a region complementary to F1 region, R1c denotes a region complementary to R1 region, and R2c denotes a region complementary to R2 region.

Examples of F1c regions may include F1c-1 to F1c-3 as described below.

F1c-1: a region complementary to the 881st to 901st regions of SEQ ID NO: 1 (SEQ ID NO: 2)

F1c-2: a region complementary to the 881st to 898th regions of SEQ ID NO: 1 (SEQ ID NO: 3)

F1c-3: a region complementary to the 881st to 899th regions of SEQ ID NO: 1 (SEQ ID NO: 4)

Examples of F2 regions may include F2-1 and F2-2 as described below.

F2-1: the 830th to 848th regions of SEQ ID NO: 1 (SEQ ID NO: 5)

F2-2: the 830th to 849th regions of SEQ ID NO: 1 (SEQ ID NO: 6)

Examples of R1 regions may include R1-1 and R1-2 as described below.

R1-1: the 911st to 931st regions of SEQ ID NO: 1 (SEQ ID NO: 7)

R1-2: the 913rd to 931st regions of SEQ ID NO: 1 (SEQ ID NO: 8)

Examples of R2c regions may include R2c-1 to R2c-4 as described below.

R2c-1: a region complementary to the 956th to 974th regions of SEQ ID NO: 1 (SEQ ID NO: 9)

R2c-2: a region complementary to the 954th to 972nd regions of SEQ ID NO: 1 (SEQ ID NO: 10)

R2c-3: a region complementary to the 958th to 974th regions of SEQ ID NO: 1 (SEQ ID NO: 11)

R2c-4: a region complementary to the 957th to 974th regions of SEQ ID NO: 1 (SEQ ID NO: 12)

Examples of F3 regions may include F3-1 as described below.

F3-1: the 798th to 817th regions of SEQ ID NO: 1 (SEQ ID NO: 13)

Three types of primers such as (FIP (forward inner primer), RIP (reverse inner primer), and F3P (forward outer primer)) can be designed on the basis of the above-mentioned five regions.

FIP is designed to consist of a base sequence that is substantially identical to F2 (hereinafter referred to as an F2 sequence) at the 3' end and a base sequence that is substantially identical to F1c (hereinafter referred to as an F1c sequence) at the 5' end. In the case of FIP, a sequence independent of CEAmRNA (hereinafter referred to as an intervening sequence) may intervene between the F2 sequence and the F1c sequence. In the case where the intervening sequence exists in FIP, the length of intervening sequence is preferably 1 to 100 bases, more preferably 1 to 50 bases.

Examples of FIP may include FIP-1 (SEQ ID NO: 14) to FIP-4 (SEQ ID NO: 17) as described below.

```
                                               (SEQ ID NO: 14)
FIP-1: CTTGGCACGTATAGGATCCACTCCAGCAATCCACCCAAGA (SEQ ID NO: 15)
FIP-2: GGCACGTATAGGATCCACTCCAGCAATCCACCCAAGA (SEQ ID NO: 16)
FIP-3: TGGCACGTATAGGATCCACTCCAGCAATCCACCCAAGA (SEQ ID NO: 17)
FIP-4: CTTGGCACGTATAGGATCCACTCCAGCAATCCACCCAAGAG
```

RIP is designed to consist of a base sequence that is substantially identical to R2c (hereinafter referred to as an R2c sequence) at the 3' end and a base sequence that is substantially identical to R1 (hereinafter referred to as an R1 sequence) at the 5' end. In the case of RIP like that of FIP, the intervening sequence may exist between the R2c sequence and the R1 sequence.

Examples of RIP may include RIP-1 (SEQ ID NO: 18) to RIP-5 (SEQ ID NO: 22) as described below.

```
                                               (SEQ ID NO: 18)
RIP-1: CAGACACTGGCCTCAATAGGAGGTTTGGGTGGCTCTGCAT (SEQ ID NO: 19)
RIP-2: CAGACACTGGCCTCAATAGGATTTGGGTGGCTCTGCATAG (SEQ ID NO: 20)
RIP-3: CAGACACTGGCCTCAATAGGAGGTTTGGGTGGCTCTGC (SEQ ID NO: 21)
RIP-4: GACACTGGCCTCAATAGGAGGTTTGGGTGGCTCTGCAT (SEQ ID NO: 22)
RIP-5: CAGACACTGGCCTCAATAGGAGGTTTGGGTGGCTCTGCA
```

F3P is designed to consist of a base sequence that is substantially identical to F3.

Examples of F3P may include F3P-1 (SEQ ID NO: 13) as described below.

F3P-1: TGCACAGTACTCTTGGTTTG (SEQ ID NO: 13)

When the RT-LAMP method is performed with a primer of the embodiment, amplification reactions of nucleic acid are carried out according to the steps described in US20040175729. Specifically, nucleic acid amplifications are carried out according to the following steps of 1) to 5).

1) RIP is hybridized to CEAmRNA (hereinafter referred to as a template RNA) which can serve as a template to form a complementary strand (RIP and an elongated strand from RIP: hereinafter referred to as a RIP strand). The synthetic reaction of a RIP strand can be performed using an enzyme which has reverse transcription activity, such as AMV Reverse Transcriptase derived from Avian Myeloblastosis Virus. Here, it is preferable to use the reverse transcriptase which has reverse transcription activity and RNase activity like that of AMV Reverse Transcriptase.

2) Next, the RIP strand which forms a double strand with mRNA is converted to a single strand. For example, a template RNA of the RIP strand is degraded by the reverse transcriptase which has the RNase activity described above, thus the RIP strand becomes a single strand. When the reverse transcriptase does not have RNase activity, it is preferable to additionally use an enzyme which has RNase activity. The RIP strand can also be converted to a single strand using a primer (R3P) which hybridizes to a downstream region than the R2 region. The obtained single RIP strand forms a loop structure at the 5' end.

3) Henceforth, the synthetic reactions of elongated strands are based on strand displacement DNA polymerase. Bst DNA Polymerase Large Fragment derived from Bacillus stearothermophilus, and the like can be used as strand displacement DNA polymerase. FIP is hybridized to the RIP strand to synthesize a complementary strand, and then the RIP strand forms a double strand with a complementary strand containing FIP (FIP and an elongated strand from FIP: hereinafter referred to as a FIP strand).

4) F3P is hybridized to the RIP strand which forms a double strand with a FIP strand, and then a complementary strand is synthesized. As a result, the complementary strand containing F3P forms a double strand with the RIP strand, and the FIP strand becomes a single strand. The obtained single FIP strand forms loop structures at both ends (the 5' and 3' end).

5) Through the activity of strand displacement DNA polymerase, a complementary strand is synthesized from the FIP strand in which the both ends have loop structures using itself as a template, and then it forms a hairpin-like structure. RIP is hybridized to the loop structure, and then a complementary strand is synthesized, which leads to dissociation of the double strand portion of the hairpin strand. Thus, a single strand is formed. This single strand forms a loop structure, and then a complementary strand is synthesized from the 3' end using itself as template. Further, FIP is hybridized to the loop structure, and then a complementary strand is synthesized.

Nucleic acid amplifications proceed by repeating such synthetic reactions.

As used herein, the term "elongated strand" refers to a polynucleotide successively synthesized by a DNA polymerase, starting from the 3' end of a primer which is hybridized to RNA or DNA.

In the above-mentioned reaction, two kinds of enzymes such as a reverse transcriptase and a DNA polymerase are used. Here, when an enzyme which has both reverse transcription activity and DNA polymerase activity (for example Bca DNA polymerase derived from Bacillus caldotenax) is used, the synthetic reaction of the above-mentioned elongated strand can be performed with one enzyme.

In the LAMP method, using loop primers (LPF and/or LPR) together with the FIP, RIP, and F3P allows for providing the starting points synthesis, which results in more rapid amplification of DNA (PCT International publication No. WO 02/24902). A region (LF) to which a loop primer can hybridize in a FIP strand is contained in a region between the 3' end of a F1c sequence and the 5' end of a F1 region. A region (LR) to which a loop primer can hybridize in a RIP strand is a region between the 3' end of a R1 sequence and the 5' end of a R1c region.

The above-mentioned region can be indicated by a region on the base sequence according to SEQ ID NO: 1, or a region on a base sequence complementary to a base sequence according to SEQ ID NO: 1.

Examples of LF may include LF-1 as described below.

A region complementary to the 970th to 988th regions of SEQ ID NO: 1 (SEQ ID NO: 23)

Examples of LR may include LR-1 to LR-3 as described below.

LR-1: the 1048th to 1065th regions of SEQ ID NO: 1 (SEQ ID NO: 24)

LR-2: the 1047th to 1065th regions of SEQ ID NO: 1 (SEQ ID NO: 25)

LR-3: the 1048th to 1066th regions of SEQ ID NO: 1 (SEQ ID NO: 26)

Loop primers can be designed on the basis of the above-mentioned regions. LPF is designed to consist of a base sequence that is substantially identical to LF. LPR is designed to consist of a base sequence that is substantially identical to LR.

Examples of LPF may include LPF-1 (SEQ ID NO: 23) as described below.

```
                                    (SEQ ID NO: 23)
LPF-1:  TCACAGTGATGTTGGGGAT
```

Examples of LPR may include LPR-1 (SEQ ID NO: 24) to LPR-3 (SEQ ID NO: 26) as described below.

```
                                    (SEQ ID NO: 24)
LPR-1:  ACAGTCACGACGATCACA
                                    (SEQ ID NO: 25)
LPR-2:  CACAGTCACGACGATCACA
                                    (SEQ ID NO: 26)
LPR-3:  ACAGTCACGACGATCACAG
```

As used herein, the term "substantially identical" or "substantially complementary" does not mean that each term is defined as completely identical or completely complementary. For example, polynucleotide B which can hybridize with a certain polynucleotide A can be said to be substantially complementary to polynucleotide A. That is, polynucleotide B does not need to be completely complementary to polynucleotide A. So long as the polynucleotide B can hybridize with the polynucleotide A, mutation, such as substitution, delition, insertion, and addition, of one or more may be included. More specifically, a percentage of mutation such as substitution, delition, insertion, and addition, of nucleotides is 20% or less, preferably 10% or less, particularly preferably 5% or less.

The regions (F1, F1c, R1, R1c, F2, F2c, R2, R2c, F3, LF, or LR) to which primers are hybridized are preferably selected in consideration of the base composition, the GC content, the secondary structure, the melting temperature (Tm), and the like. Generally, the Tm can be calculated by the Nearest Neighbor method. Preferably, the Tm is in the range of 55 to 65° C., more preferably in the range of 58 to 64° C. The GC content is preferably in the range of 40 to 70%, more preferably in the range of 50 to 65%. Preferably, 3 mer at the 3' end of primer is completely complementary to a region to be hybridized, more preferably 5 mer at the 3' end of primer is completely complementary to a region to be hybridized.

The chain length of primer used in the invention is not particularly limited as long as the length is sufficient to be hybridized to RNA or DNA. Preferably, the length is 5 to 200 bases, more preferably 10 to 50 bases. The chain length of primer which can be recognized by known polymerases which catalyze sequence-dependent nucleic acid synthesis is at least around 5 bases. Therefore a preferable chain length of the portion to be hybridized is more than that. In addition, in order to maintain the specificity of a base sequence, the length is preferably 10 bases or more. On the one hand, since a very long primer is difficult to prepare by chemical synthesis, the chain length as described above is preferable.

Since the primer mentioned above is used for amplification reactions with CEAmRNA as a template, the primer is preferably designed not to perform amplification reaction of the CEA gene of genome.

In the embodiment, with reference to CEAmRNA, a region corresponding to the 4th exon (the 704th to 958th of SEQ ID NO: 1) of a CEA gene is designated as the region corresponding to the fourth exon, and a region corresponding to the fifth exon (the 959th to 1237th of SEQ ID NO: 1) of a CEA gene is designated as a region corresponding to the fifth exon. Preferably, at least one of primers mentioned above is hybridized to a region containing a linkage site between the region corresponding to the fourth exon and the region corresponding to the fifth exon. The region containing the linkage means the region containing the nucleotide at the 3' end of region corresponding to the fourth exon and nucleotide at the 5' end of region corresponding to the fifth exon. When such primers are used, DNA of the sequence from CEA gene is poorly amplified. Therefore, it is possible to selectively amplify DNA of the sequence from CEA mRNA.

Nucleic acid amplification primer in the embodiment has a sequence which can be hybridized to a first target region consisting of the region corresponding to the fourth exon and the region corresponding to the fifth exon, or a second target region complementary to the first target region. Primers may contain at least three kinds of primers such as FIP, RIP, and F3P, and further may contain LPF and/or LPR. The respective primers may contain sequences subjected to mutation such as substitution, delition, insertion, and addition of one or more nucleotides as long as they have a function of primer.

The term "a function of primer" means a function in which a polynucleotide is hybridized to a target sequence under stringent hybridization conditions and then it can become a synthetic starting point for the nucleic acid synthesis reaction by a polymerase.

The term "stringent hybridization condition" refers to the condition in which hybridization takes place at about 5° C. to 30° C. below the melting temperature (Tm), preferably at about 10° C. to 25° C. below the melting temperature. The stringent hybridization condition can be controlled by varying formamide concentration, concentration, chaotropic salt concentration, pH (hydrogen ion concentration), the composition of an organic solvent, and the like. One example of stringent hybridization conditions include the condition in which hybridization is performed in a solution containing 50% formamide, 5×SSC (150 mM NaCl, 15 mM trisodium citrate), 50 mM sodium phosphate, pH of 7.6, 5×Denhardt's solution, 10% dextran sulfate, and 20 µg/ml of DNA at 42° C. overnight.

Primers can be prepared by known methods. Specifically, a high-throughput nucleic acid synthesizer such as ABI 3900 High-Throughput DNA Synthesizer can be used to synthesize primers.

(Primer Set)

When the RT-LAMP method is performed using primers of the embodiment, a combination of at least three kinds of primers (FIP, F3P, and RIP) can be used as a primer set. In addition, a combination of one or more kinds of loop primers can be used as a primer set.

Examples of primer sets consisting of three kinds of primers include a primer set which has a first primer consisting of SEQ ID NO: 14, a second primer consisting of SEQ ID NO: 18, and a third primer consisting of SEQ ID NO: 13.

When a combination of five kinds of primers is used as a primer set, specifically examples of primer sets include primer sets A to J shown the following Table 1. Each number in Table 1 indicates SEQ ID NOs.

TABLE 1

| Kinds of primers | Primer set | | | | | | | | | |
|---|---|---|---|---|---|---|---|---|---|---|
| | A | B | C | D | E | F | G | H | I | J |
| FIP | 14 | 16 | 15 | 15 | 15 | 15 | 15 | 15 | 17 | 15 |
| RIP | 18 | 18 | 19 | 20 | 21 | 18 | 18 | 18 | 18 | 22 |
| F3P | 13 | 13 | 13 | 13 | 13 | 13 | 13 | 13 | 13 | 13 |
| LPF | 23 | 23 | 23 | 23 | 23 | 23 | 23 | 23 | 23 | 23 |
| LPR | 24 | 24 | 24 | 24 | 24 | 25 | 26 | 24 | 24 | 24 |

(Measuring Method)

In the LAMP method, since an amount of magnesium pyrophosphate which is produced as a by-product in process of amplification is large, a white tuvidity is formed. Therefore, the results of amplification reactions based on mRNA can be given by inspecting turbidity of this reaction solution with the naked eye or, by measuring the turbidity using the scattered light intensity from the reaction solution and the intensity ratio between the transmitted and scattered light.

Most of the DNA strand synthesized by the LAMP method is a double-stranded DNA. It is possible to measure results of the amplification reactions based on mRNA using this characteristic. When nucleic acid amplifications are performed in the presence of fluorochrome dyes such as ethidium bromide, SYBR Green I, or Pico Green, the fluorescence intensity increased with the increase in amplified products is observed. Monitoring fluorescence intensity in real time allows tracing of amplified DNA based on mRNA in a closed system and increased fluorescence at the same time.

(Reagent Kit)

Reagents used in the embodiment can also be provided as a reagent kit. The reagent kit includes enzymers including dNTPs (deoxynucleoside triphosphate including DATP, dCTP, dGTP, and dTTP), an enzyme having reverse transcription activity and a DNA polymerase used as a substrate for synthesis of complementary strands, and a primer. Further, it is preferred that the reagent kit includes a reagent with which a reaction solution can be suitably prepared for amplification reactions. It is also preferable that the reagent kit includes an enzyme which has RNase activity. Primers may be provided as a solution by previously dissolving in a solvent such as TE buffer, or may be provided in the dry state.

Table 2 shows composition of reaction solutions used for the RT-LAMP reaction. For example, when the reaction reagents, primer solutions, and enzymes shown in Table 2 are provided as a reagent kit, the reaction reagents and primer solutions can be placed in the same container, and only enzymes can be placed in another container.

Further, buffer agents with which pH of a reaction solution can be adjusted in the desired range, salts which can maintain the catalytic activity of enzymes, enzyme protective agents, melting temperature-regulating agents, and the like can be used. Buffer agents are not particularly limited as long as the pH of the reaction solution can be adjusted, preferably in the range of 6.0 to 8.0, more preferably in the range of 6.5 to 7.5. For example, HEPES (N-2-hydroxyethlpiperazine-N'-2'-ethanesulfonic-acid) and Tris-HCl can be used. Examples of salts used in the invention include $(NH_4)_2SO_4$, KCl, HCl, NaCl, and the like. Examples of protective agents for enzymes used in the invention include Triton-X and bovine serum albumin, and the like. Examples of melting temperature-regulating agents used in the invention include DMSO (dimethyl sulfoxide), betaine (N, N, N, -trimethylglycine), and the like. The above-mentioned reagents can be properly selected according to the kind of enzyme used for the regulation of the Tm or reaction. Therefore, when a reaction solution is properly prepared for amplification reactions, all reagents described above do not need to be contained in the reaction solution.

TABLE 2

| | | | |
|---|---|---|---|
| Reaction solutions | Pure water | Eppendorf | 4.21 μl |
| | 1 M Tris-HCl (pH8.0) | NIPPON GENE | 0.75 μl |
| | 10× Thermopol buffer | New England | 2.50 μl |
| | 10 mM d NTPs solution | Invitrogen | 2.00 μl |
| | 100 mM MgSO4 solution | Nacalai Tesque | 0.75 μl |
| | 100 mM DTT solution | SIGMA | 1.25 μl |
| | 2% Tergitol | SIGMA | 2.50 μl |
| | Rnasin Plus Rnase Inhibitor | Promega | 0.63 μl |
| Primer solution | FIP solution (80 pmol/μl) | Invitrogen | 1.00 μl |
| | RIP solution (80 pmol/μl) | Invitrogen | 1.00 μl |
| | F3P solution (5 pmol/μl) | Invitrogen | 1.00 μl |
| | LPF solution (60 pmol/μl) | Invitrogen | 1.00 μl |
| | LPR solution (60 pmol/μl) | Invitrogen | 1.00 μl |
| Enzymes | AMV Reverse Transcriptase (10 U/μl) | Promega | 0.14 μl |
| | Bst DNA Polymerase Large Fragment (8 U/μl) | New England | 2.27 μl |
| Template solution | | | 2.00 μl |
| Total Volume | | | 24.00 μl |

10× Thermopol buffer in Table 2 contains 1.0% Triton-X. Triton-X is a nonionic surfactant, which helps to maintain a tertiary structure of enzyme and keeps it stable. When a surfactant is heated until a temperature reaches a certain temperature (clouding point), the turbidity is produced. This clouding point varies depending on surfactants. Since 1.0% Triton-X has a clouding point lower than the reaction temperature (65° C.) of nucleic acid amplification described later, it reaches a clouding point as nucleic acid amplification reaction in the embodiment is performed. To avoid this problem, it is preferable to add a surfactant which can raise the clouding point of a reaction solution (clouding point due to a surfactant originally contained in the reaction solution) higher than the reaction temperature of nucleic acid amplification. Such surfactants include a surfactant which has a clouding point higher than the reaction temperature, and preferably a surfactant which has a clouding point of 70° C. or more.

Large amounts of RNase contain in the biological samples, and thus mRNA used as a template in the biological samples may be degraded. Therefore, the reagent kit preferably includes an inhibitor of RNase derived from this biological samples. However, it is preferable that the inhibitor used in the invention inhibits the RNase activity in the biological samples and does not inhibit the RNase activity of the aforementioned reverse transcriptase that has RNase activity.

Biological samples such as tissue, expectoration, urine, biopsy, coelomic fluid, or coelome lavage fluid can be used. Examples of tissues include blood, lymph, lymph node, the tissue section of large intestine or stomach, and the like. Examples of coelomic fluids include ascitic fluid, pleural fluid, and the like. Examples of coelome lavage fluids include intraabdominal lavage fluid, thoracic lavage fluid, and the like. A biological sample treatment solution which will be described later is added to the biological samples, which is homogenized. Thereafter, mRNA is extracted and purified using for example RNeasy Kit (Quiagen), TRIZOL Reagent (invitrogen), or the like, and which can be used as a template solution.

The above-mentioned template solution, enzyme having reverse transcription activity, dNTPs, strand displacement DNA polymerase, and primer sets of the embodiment are mixed, which can be used to prepare the reaction solutions used for the RT-LAMP method. The amplification reactions based on CEAmRNA are performed by heating this reaction solution and thus CEAmRNA in the biological samples can be detected.

(Assistance of Cancer Diagnosis)

Information for assisting cancer diagnosis can be provided on the basis of the detection results of CEAmRNA. Examples of cancers include rectal cancer, colonic cancer, gastric cancer, esophagus cancer, lung cancer, mammary cancer, liver cancer, biliary tract cancer, pancreas cancer, thyroid cancer, bladder cancer, prostate cancer, scrotal cancer, cervix cancer, cancer of uterine body, cervical cancer, ovarian cancer, and the like.

Examples of Information for assisting cancer diagnosis include the presence of CEAmRNA in biological samples, the time until the concentration (turbidity) of amplified products by amplification reactions based on CEAmRNA reaches a predetermined value (detection time), the concentration (turbidity) of amplified products which reaches the value within a predetermined time, the copy number of CEAmRNA calculated by the detection time, or the like. On the basis of the above-mentioned information, the presence or content of cancer cells in the biological samples, and the like can be provided as information for assisting cancer diagnosis.

A health care professional such as a medical doctor can determine the presence of minute metastases in the biological samples and the level of metastasis in the case of presence of metastases using the information relevant to cancer diagnosis. Further, using Information for assisting cancer diagnosis allows assessment of the possibility of metastasis and recurrence, poor prognosis, susceptibility to anticancer agents.

A preferable method to obtain information for assisting cancer diagnosis from results after performing the RT-LAMP is to compare the detection results of CEAmRNA with the threshold previously determined. For example, the detection time of amplification products in amplification reactions based on CEAmRNA is measured after performing the RT-LAMP. Then the resulting detection time is compared with the corresponding threshold and the comparison results can be used as information for assisting cancer diagnosis. The concentration (turbidity) of amplification products in amplification reactions based on CEAmRNA is measured after performing the RT-LAMP within a predetermined time. Then the resulting concentration (turbidity) is compared with the corresponding threshold, and the comparison results can provide information for assisting cancer diagnosis. Alternately, the copy number of mRNA is calculated from the detection time, and the given copy number may be compared with the corresponding threshold.

For example, the threshold corresponding to the detection time can be set as follows. First, the detection time is measured using specimens containing a large number of cancer cells (cancer-positive samples). Next, the detection time is measured using specimens not containing a large number of cancer cells (cancer-negative samples). A value which is longer than the detection time of cancer-positive samples and shorter than the detection time of cancer-negative samples can be defined as a threshold. In the case where cancer positive-samples which indicate the detection time longer than a threshold and/or cancer-negative samples which indicate the detection time shorter than a threshold are contained, the detection time in which cancer-positive samples can be distinguished from cancer-negative samples with a high probability of success can be defined as a threshold. Specimens determined to be positive by a pathologist can be used as cancer-positive samples. Specimens taken from cancer-negative patients can be used as cancer negative samples. Here, specimens taken from cancer-positive patients can also be used as long as they are determined to be negative by a pathologist.

Obtaining the above Information for assisting cancer diagnoses during surgical extirpation of cancer allows for determination of the borders of the tumor to be resected, or the range of lymph node dissection. The range of the tumor to be removed is appropriately determined during surgery and extirpation is performed, thereby avoiding further surgery because of inadequate removal of the tumor and excessive removal of normal tissue.

EXAMPLES

In the example, any of primer sets A to J in Table 1 was used as a primer set.

Example 1

An experiment whether it could be possible to detect CEAmRNA using primer sets A to J and the already reported primer set (referred to as primer set 24) was performed. The primers contained in primer set 24 were indicated in SEQ ID NOs: 27 to 32.

1) Preparation of Reaction Solutions

RT-PCR was performed using a forward primer (5' CGGAATTCATGGAGTCTCCCT 3': SEQ ID NO: 33) designed on the basis of the base sequence of CEAmRNA, an outer primer (5° CGTCTAGACTATATCAGAGCAA 3': SEQ ID NO: 34), RNAs extracted from the KATO III cells, and One-step RT-PCR Kit (QIAGEN).

The obtained amplification products and a plasmid vector, i.e. pGEM-3Z (Promega Corporation), were treated with restriction enzymes (EcoR I, Xba I), the amplification products were incorporated into pGEM-3Z using ligation kit (TAKARA) to produce a recombinant plasmid. This recombinant plasmid was transformed into *Escherichia coli*, which was cultured. After lysis of the cultured *Escherichia coli*, cDNAs corresponding to CEAmRNA (hereinafter referred to as CEAcDNA) were extracted. CEARNA having a sequence that was substantially identical to CEAmRNA was synthesized from the obtained CEAcDNA using Riboprobe in vitro transcription system (Promega Corporation). The concentration of the obtained CEARNA solution was calculated from the absorbance readings at 260 nm. Template solution a in which the number of copies of CEARNA were 10,000,000 copies per 2 µl, template solution b in which the number of copies of CEARNA were 100,000 copies per 2 µl, and template solution c in which the number of copies of CEARNA were 1,000 copies per 2 µl were diluted and prepared using 50 ng/mL yeast RNA (Ambion, Inc.) based on the concentration of CEARNA solution. The reaction solution was prepared by the composition in Table 2. 2 µl of a template solution which was selected from any of template solutions a to c was used. 2 µl of 50 ng/mL yeast RNA (Ambion, Inc.) was used as a negative control in place of template solution. Primer set 24, or any of primer sets A to J in Table 1 was used. The reaction solution containing primer set 24 was prepared according to the composition in Table 2 except that 1 µl of R3P solution (5 pmol/µl) containing R3P which was another type of outer primer different from F3P was contained and further 3.21 µl (not 4.21 µl) of pure water was contained.

2) The RT-LAMP Reaction

The reaction solutions prepared were heated at 65° C. for 20 minutes using Real time turbidimeter LA-200 (TERAMECS CO., LTD.). The same experiments were performed for all the reaction solutions 4 times.

3) Measurement of Detection Time

Time (detection time) when the turbidity of a reaction solution reached 0.1 value was measured in real time. LA-200 (TERAMECS CO., LTD.) was used for the measurements as described above.

4) Result

The results of Example 1 were indicated in Table 3.

TABLE 3

| Primer set | Template solution | a | | | | b | | | | c | | | Negative control | | |
|---|---|---|---|---|---|---|---|---|---|---|---|---|---|---|---|
| 24 | Detection time (min) | 8.7 | 8.7 | 8.7 | 8.8 | 9.7 | 9.8 | 9.8 | 9.8 | 10.9 | ND | ND | ND | ND | ND | ND | ND |
|  | AVG | | 8.7 | | | | 9.8 | | | — | | | — | | | |
| A | Detection time (min) | 8.4 | 8.3 | 8.4 | 8.4 | 9.4 | 9.5 | 9.6 | 9.6 | 10.2 | 11.1 | 10.3 | 10.8 | ND | ND | ND | ND |
|  | AVG | | 8.4 | | | | 9.5 | | | | 10.6 | | | | ND | | |
| B | Detection time (min) | 8.1 | 8.2 | 8.2 | 8.1 | 9.1 | 9.1 | 9.1 | 9.2 | 9.8 | 10.5 | 9.9 | 9.9 | ND | ND | ND | ND |
|  | AVG | | 8.2 | | | | 9.1 | | | | 10.0 | | | | ND | | |
| C | Detection time (min) | 8.3 | 8.4 | 8.4 | 8.5 | 9.6 | 9.5 | 9.6 | 9.8 | 10.9 | 10.1 | 11.1 | 11.5 | ND | ND | ND | ND |
|  | AVG | | 8.4 | | | | 9.6 | | | | 10.9 | | | | ND | | |
| D | Detection time (min) | 8.1 | 8.1 | 8.1 | 8.1 | 9.2 | 9.1 | 9.3 | 9.2 | 10.6 | 10.7 | 11.1 | 11.9 | ND | ND | ND | ND |
|  | AVG | | 8.1 | | | | 9.2 | | | | 11.1 | | | | ND | | |
| E | Detection time (min) | 8 | 8.1 | 8.1 | 8.1 | 9 | 9 | 9.1 | 9.4 | 10 | 9.9 | 10 | 11.2 | ND | ND | ND | ND |
|  | AVG | | 8.1 | | | | 9.1 | | | | 10.3 | | | | ND | | |
| F | Detection time (min) | 8.5 | 8.5 | 8.5 | 8.5 | 9.5 | 9.4 | 9.4 | 9.4 | 11.7 | 10.9 | 10.1 | 18.5 | ND | ND | ND | ND |
|  | AVG | | 8.5 | | | | 9.4 | | | | 12.8 | | | | ND | | |
| G | Detection time (min) | 8.3 | 8.3 | 8.3 | 8.2 | 9.2 | 9.2 | 9.3 | 9.2 | 14.6 | 11.3 | 10.2 | 10.2 | ND | ND | ND | ND |
|  | AVG | | 8.3 | | | | 9.2 | | | | 11.6 | | | | ND | | |
| H | Detection time (min) | 8.6 | 8.7 | 8.6 | 8.6 | 9.7 | 9.6 | 9.7 | 9.7 | 11.1 | 11.2 | 11.8 | 12.4 | ND | ND | ND | ND |
|  | AVG | | 8.6 | | | | 9.7 | | | | 11.6 | | | | ND | | |

TABLE 3-continued

| Primer set | Template solution | a | | | | b | | | | c | | | Negative control | | | |
|---|---|---|---|---|---|---|---|---|---|---|---|---|---|---|---|---|
| I | Detection time (min) | 8.1 | 8 | 8 | 8.1 | 9.1 | 9 | 9 | 9.2 | 10.2 | 10.9 | 9.7 | 10 | ND | ND | ND | ND |
| | AVG | | 8.1 | | | | 9.1 | | | | 10.2 | | | | ND | | |
| J | Detection time (min) | 8 | 7.9 | 7.9 | 7.9 | 8.9 | 9 | 9.1 | 8.8 | 10.4 | 9.7 | 10.3 | 10.3 | ND | ND | ND | ND |
| | AVG | | 7.9 | | | | 9.0 | | | | 10.2 | | | | ND | | |

AVG: Average detection time (min)
ND: not detected

In Table 3, AVG indicates an average value (minute) of the detection time measured 4 times. ND indicates that amplified DNA has been not detected within 20 minutes. As a result of the measurement using a reaction solution containing negative control, amplified DNA was not detected even though all primer sets were used. As results of the measurement using a reaction solution containing template solution c, when primer sets A to J were used DNA amplification was detected. However, when primer set 24 was used DNA amplification was detected only once during four measurements. As results of the measurement using a reaction solution containing template solution a, and the measurement using a reaction solution containing template solution b, amplified DNA was detected in each measurements. However, the detection time for primer sets A to J was shorter than that for primer set 24.

As the results described above, when primer sets A to J were used amplified DNA was detected in a reaction solution containing low RNA copy numbers as compared with primer set 24. Further, it was found that amplified DNA could be detected in a shorter time than in the case described above.

Example 2

Primer sets in the invention was used to examine the reproducibility of detection time.

Template solution d (containing 5,000 copies of CEARNA per 2 µl), template solution e (containing 2,500 copies of CEARNA per 2 µl), template solution f (containing 1,000 copies of CEARNA per 2 µl), template solution g (containing 500 copies of CEARNA per 2 µl) were diluted and prepared using a CEARNA solution obtained by the same method as Example 1 and 50 ng/mL yeast RNA (Ambion, Inc.).

2 µl of a template solution which was selected from any of template solutions e to g was used to prepare the reaction solution according to the composition in Table 2. Any of the primer set 24, primer set A shown in the Table 1, and primer set H was used for primer set. Here, a reaction solution containing primer set 24 was prepared by the same composition as Example 1. The prepared reaction solutions were heated at 65° C. for 20 minutes using LA-200 (TERAMECS CO., LTD.). The same experiments were performed for all the reaction solutions 10 times and the detection time was measured in real time.

Figure 2:
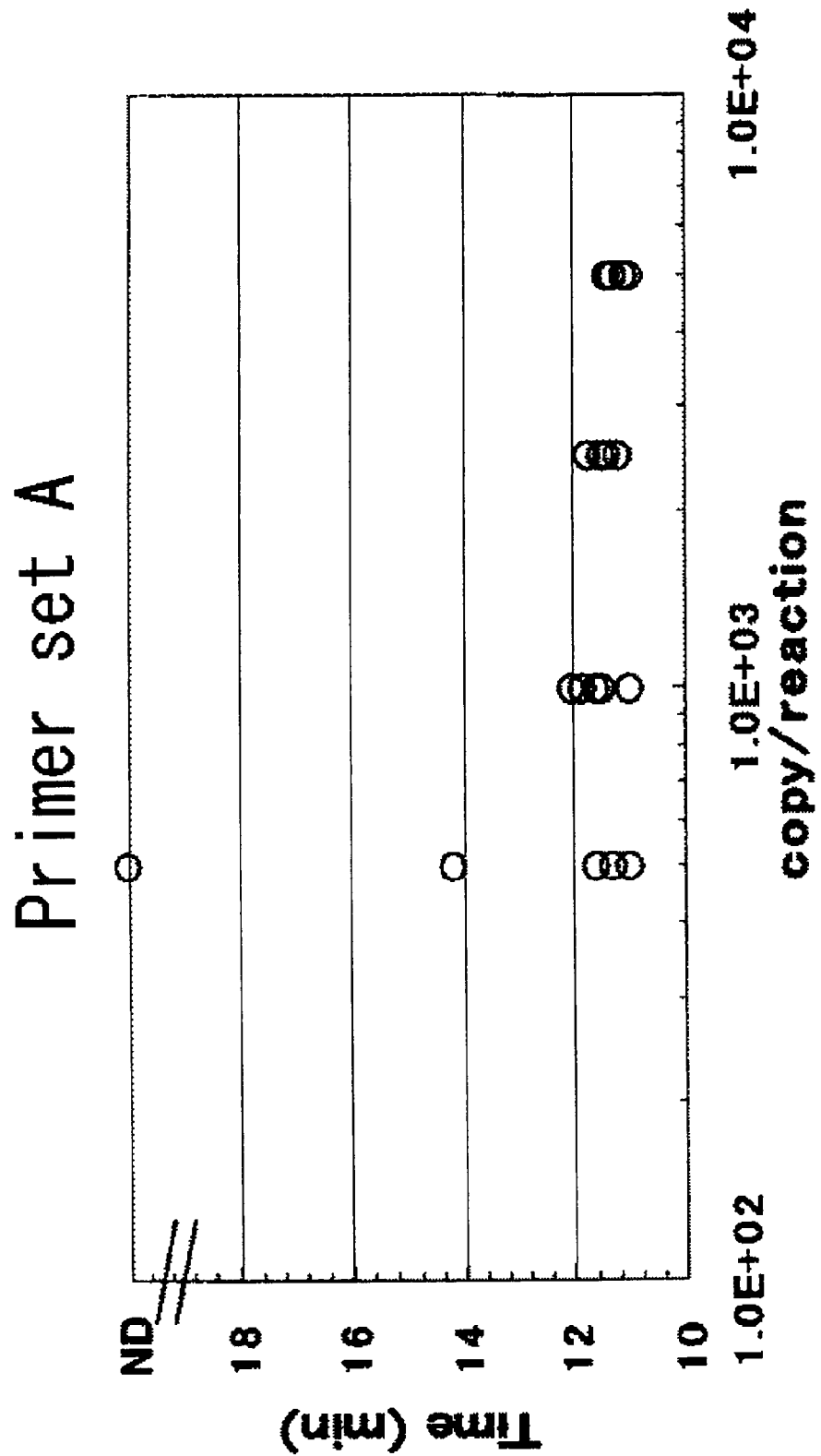
FIG. 2 is a view showing the measurement results of primer set A in Example 2.
Figure 3:
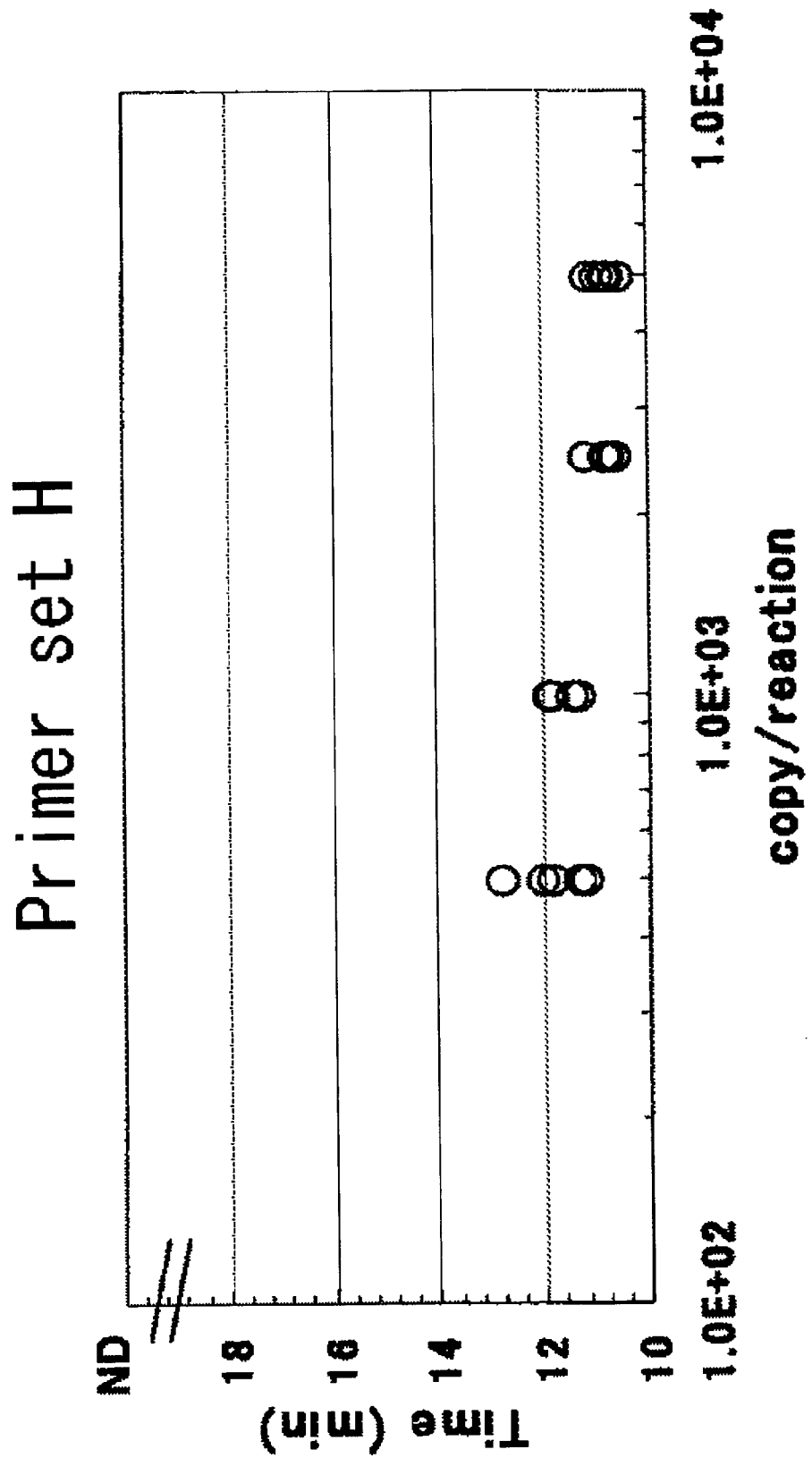
FIG. 3 is a view showing the measurement results of primer set H in Example 2.

The results of Example 2 were indicated in Table 4 and FIGS. 1 to 3.

TABLE 4

| Template solution | | d | e | f | g |
|---|---|---|---|---|---|
| Primer set 24 | 1 | 11.8 | 12.1 | 13 | ND |
| | 2 | 11.7 | 12.2 | ND | ND |
| | 3 | 11.9 | 12 | 15.3 | 16.1 |
| | 4 | 13.2 | 14.7 | 12.9 | ND |
| | 5 | 12.2 | ND | 12.5 | ND |

TABLE 4-continued

| Template solution | | d | e | f | g |
|---|---|---|---|---|---|
| | 6 | 12.3 | 12.3 | 16 | 12.2 |
| | 7 | 12.4 | 12.4 | 15.4 | 13.1 |
| | 8 | 11.9 | 11.9 | 12.1 | 12.5 |
| | 9 | 12.1 | 12.1 | 12.9 | 13.1 |
| | 10 | 11.8 | 11.8 | 13.9 | 13.4 |
| | AVG | 12.16 | — | — | — |
| | CV | 5.02 | — | — | — |
| primer set A | 1 | 11.1 | 11.4 | 11.5 | 11.3 |
| | 2 | 11.3 | 11.2 | 12 | 14.2 |
| | 3 | 11.4 | 11.5 | 11.6 | ND |
| | 4 | 11 | 11.5 | 11 | 11.6 |
| | 5 | 11.1 | 11.7 | 11.8 | 11 |
| | 6 | 10.9 | 11.3 | 16.3 | 14.2 |
| | 7 | 11.8 | 11.1 | 11.8 | 12.1 |
| | 8 | 11.2 | 11.6 | 11.8 | 11 |
| | 9 | 11 | 11.1 | 11.5 | 12.4 |
| | 10 | 11 | 11.2 | 11.9 | 12.3 |
| | AVG | 11.18 | 11.46 | 11.58 | — |
| | CV | 1.47 | 1.59 | 3.25 | — |
| primer set H | 1 | 10.8 | 10.7 | 11.3 | 11.8 |
| | 2 | 11.1 | 11.2 | 11.8 | 11.3 |
| | 3 | 10.9 | 10.6 | 11.9 | 12.8 |
| | 4 | 10.5 | 10.8 | 11.4 | 11.2 |
| | 5 | 10.7 | 10.8 | 11.3 | 12 |
| | 6 | 10.5 | 11 | 11.1 | 12.2 |
| | 7 | 10.6 | 10.7 | 11.1 | 12.1 |
| | 8 | 11.1 | 11.2 | 12.1 | 11 |
| | 9 | 10.5 | 11.5 | 11.1 | 13.6 |
| | 10 | 11 | 11.6 | 11.1 | 12 |
| | AVG | 10.80 | 10.82 | 11.54 | 11.82 |
| | CV | 2.07 | 2.11 | 2.50 | 5.43 |

ND: not detected
AVG: Average detection time (min)
CV: coefficient of varidation CV (coefficient of variation) in Table 4 is an index of relative spread of measurements of the detection time, and is calculated from the mean and standard deviation of the detection time. ND indicated amplified DNA was not detected within 20 minutes. The ordinate shown FIG. 1 to 3 indicates the detection time and the abscissa indicates the number of copies of CEARNA. As a result of the measurement using a reaction solution containing template solution e, CV value was 5% or more in the case of primer set 24. However, the low CV values were obtained, i.e. 1.47% for primer set A and 2.07% for primer set H. As results of the measurement using a reaction solution containing template solution f, when primer set 24 was used there were some cases where amplified DNA was not detected. However, when primer sets A and H were used amplified DNA was detected in 10 measurements. The low CV values were obtained, i.e. 1.59% for primer set A and 2.11% for primer set H. As results of the measurement using a reaction solution containing template solution g, when primer set 24 was used there were some cases where amplified DNA was not detected. However, when primer set A and H were used amplified DNA was detected in 10 measurements. The low CV values were obtained, i.e. 3.25% for primer set A and 2.50% for primer set H. As results of the measurement using a reaction solution containing template solution h, when primer set 24 was used amplified DNA could not detected 4 times out of 10. However, when primer set A was used amplified DNA could be detected 9 times out of 10 and when primer set H was used amplified DNA could be detected in 10 measurements. From the above measurement results, it was found that the results using primer set A and H showed good reproducibility of detection time as compared with the result using primer set 24.

Example 3

The amplification based on CEARNA was detected in the amplification reaction using primer set not containing loop primer. A reaction solution was diluted so as to contain 5,000 CEARNA copies per 2 µl using a CEARNA solution obtained by the same method as Example 1 and 50 ng/mL yeast RNA (Ambion, Inc.), and then template solution was obtained. A mixed solution containing pure water, reaction reagents, and enzymes (shown in Table 2) were prepared using 2 µl of this template solution.

Each primer was added to this mixed solution according to Table 5, and reaction solutions I to IV were prepared. First, 80 pmol of FIP-1 (SEQ ID NO: 14), 80 pmol of RIP-1 (SEQ ID NO: 18), and 5 pmol of F3P-1 (SEQ ID NO: 13) were added to reaction solutions I to IV. Next, 60 pmol of LPF-1 (SEQ ID NO: 23) was only added to reaction mixture II. 60 pmol of LPR-1 (SEQ ID NO: 24) was only added to reaction mixture III. 60 pmol of LPF-1 and LPR-1 were added to reaction mixture IV. The reaction solutions I to IV were prepared and then heated at 65° C. for 30 minutes using Real time turbidimeter LA-200 (TERAMECS CO., LTD.). The same experiments were performed for all the reaction solutions 4 times and the detection time was measured in real time. The average of detection time was indicated in Table 5.

TABLE 5

| | | Reaction solution | | | |
|---|---|---|---|---|---|
| | | I | II | III | IV |
| Concentrations of primer (pmol) | FIP-1 | 80 | 80 | 80 | 80 |
| | RIP-1 | 80 | 80 | 80 | 80 |
| | F3P-1 | 5 | 5 | 5 | 5 |
| | LPF-1 | 0 | 60 | 0 | 60 |
| | LPR-1 | 0 | 0 | 60 | 60 |
| AVG | | 28.1 | 12.1 | 12.6 | 8.7 |

AVG: Average detection time (min)

As shown in Table 5, the detection time was 28.1 minutes when a reaction solution I used. The detection time of a reaction solution containing LPF-1 was 12.1 minutes. The detection time of a reaction solution containing LPR-1 was 12.6 minutes. The detection time of a reaction solution containing LPF-1 and LPR-1 was 8.7 minutes. From the above results, it was found that amplification of CEAcDNA was detected in the reaction solution not containing loop primer.

Example 4

The inventors examined whether it could be possible to specifically detect CEAmRNA in a clinical sample using primer set of the invention. The three samples of lymph node (samples 1, 2, and 3) which were histologically confirmed to be positive in colon cancer metastasis, and the three samples of lymph node 3 (samples 4, 5, and 6) which were confirmed to be negative in colon cancer metastasis were used as clinical samples. biological sample treatment solutions (containing 200 mM Glicine-HCl, 5% Brij35 (Polyoxyethylene(23) Lauryl Ether), 20% DMSO, and 0.05% KS-538 (Shin-Etsu Chemical Co., Ltd.)) were added to samples 1 to 6, respectively and homogenized using an electric homogenizer. RNAs were extracted from the homogenized biological samples and purified using RNeasy Kit (Quiagen). Next, the resulting extracts were diluted 10-fold with the biological sample treatment solutions and template solutions 1 to 6 were obtained. Any of template solutions 1 to 6, primer set A, or H was used to prepare the reaction solution according to the composition in Table 2.

With reference to a reaction solution using primer set A, a reaction solution containing template solution 1 was designated as reaction solution A1, a reaction solution containing template solution 2 was designated as reaction solution A2, a reaction solution containing template solution 3 was designated as reaction solution A3, a reaction solution containing template solution 4 was designated as reaction solution A4, a reaction solution containing template solution 5 was designated as reaction solution A5, and a reaction solution containing template solution 6 was designated as reaction solution A6. With reference to a reaction solution using primer set H, a reaction solution containing template solution 1 was designated as reaction solution H1, a reaction solution containing template solution 2 was designated as reaction solution H2, a reaction solution containing template solution 3 was designated as reaction solution H3, a reaction solution containing template solution 4 was designated as reaction solution H4, a reaction solution containing template solution 5 was designated as reaction solution H5, and a reaction solution containing template solution 6 was designated as reaction solution H6. Negative controls were prepared according to the composition in Table 2 using 2 µl of the biological sample treatment solution in place of template solution. A negative control containing primer set A was designated as negative control A (NA), and a negative control containing primer set H was designated as negative control H (NH).

Reaction solutions A1 to A6, reaction solutions H1 to H6, NA, and NH were heated at 65° C. for 30 minutes using GD-100 Gene Amplification Analyzer (SYSMEX CORPORATION), and the detection time was measured in real time. The same experiments were performed for all the reaction solutions 4 times.

The results of measurements were indicated in Table 6 and 7.

TABLE 6

| Reaction solution | Detection time (min) | | | | AVG |
|---|---|---|---|---|---|
| A1 | 9.4 | 9.1 | 9.3 | 9.4 | 9.30 |
| A2 | 9.3 | 9.4 | 9.2 | 9.2 | 9.28 |
| A3 | 9.3 | 9.3 | 9.2 | 9.2 | 9.25 |
| A4 | ND | ND | ND | ND | — |
| A5 | ND | ND | ND | ND | — |
| A6 | ND | ND | ND | ND | — |
| NA | ND | ND | ND | ND | — |

NA: Negative control A
AVG: Average detection time (min)
ND: not detected

TABLE 7

| Reaction solution | Detection time (min) | | | | AVG |
|---|---|---|---|---|---|
| H1 | 9.2 | 9.0 | 9.1 | 9.2 | 9.13 |
| H2 | 9.4 | 9.3 | 9.1 | 9.1 | 9.23 |

TABLE 7-continued

| Reaction solution | Detection time (min) | | | | AVG |
|---|---|---|---|---|---|
| H3 | 8.7 | 8.8 | 8.9 | 8.8 | 8.80 |
| H4 | 28.7 | ND | ND | ND | — |
| H5 | ND | ND | ND | ND | — |
| H6 | ND | ND | ND | ND | — |
| NH | ND | ND | ND | ND | — |

NH: Negative control H
AVG: Average detection time (min)
ND: not detected

Table 6 shows the measurement results using primer set A. Table 7 shows the measurement results using primer set H. ND indicated amplified CEAmRNA was not detected within 30 minutes.

As results of the measurement using reaction solutions A1 to A3 and reaction solutions H1 to H3, the amplification based on CEAmRNA was detected for all the reaction solutions, and CEAmRNA contained in cancer cells was specifically detected.

As results of the measurement using reaction solutions A4 to A6, the amplification based on CEAmRNA was not detected for all the reaction solutions.

As results of the measurement using reaction solutions H5 and H6, the amplification based on CEAmRNA was not detected for all the reaction solutions.

As results of the measurement using reaction solution H4, the amplification based on CEAmRNA was detected once out of 4. The detection time was 28.7 minutes.

The threshold of the detection time in this example was 20 minutes. Samples 1, 2, and 3 (samples of lymph node) could be determined to be positive in cancer metastasis and samples 4, 5, and 6 (samples of lymph node) could be determined to be negative in cancer metastasis by comparing this threshold with the above-mentioned measurement results.

From the above results, it was confirmed that the presence of the cancer cells contained in clinical samples was determined using primer sets of the embodiment, thereby determining whether there was lymph node metastasis and the obtained results could be provided as information for assisting cancer diagnosis.

The foregoing detailed description and examples have been provided by way of explanation and illustration and are not intended to limit the scope of the appended claims. Many variations in the presently preferred embodiments will be obvious to one of ordinary skill in the art, and remain within the scope of the appended claims and their equivalents.

What is claimed is:

1. A nucleic acid amplification primer set for detecting mRNA of carcinoembryonic antigen (CEA) comprising a first primer consisting of the sequence of SEQ ID NO: 15, a second primer consisting of the sequence of SEQ ID NO: 18, a third primer consisting of the sequence of SEQ ID NO:13, a fourth primer consisting of the sequence of SEQ ID NO: 23, and a fifth primer consisting of the sequence of SEQ ID NO: 24.

2. A reagent kit for detecting mRNA of CEA comprising the nucleic acid amplification primer set according to claim 1, an enzyme having reverse transcription activity, dNTPs, and strand displacement DNA polymerase.

3. A method for assisting cancer diagnosis comprising the steps of:
   preparing reaction solutions by mixing biological samples collected from individuals, an enzyme having reverse transcription activity, dNTPs, strand displacement DNA polymerase, and the nucleic acid amplification primer set according to claim 1;
   heating the reaction solution in order to allow amplification reaction based on mRNA of CEA using the primer set; and
   measuring the amplification to determine whether mRNA of CEA is present in the biological sample based on measurement results.

4. The method as set forth in claim 3, wherein the amplification is measurement of the turbidity of a reaction solution in the step, and the time until the turbidity of reaction solution reaches a predetermined value and the turbidity of reaction solution which reaches the value within a predetermined time are measured, and the determination is achieved on the basis of the obtained time and turbidity.

5. The method as set forth in claim 3, wherein the biological sample is tissue, expectoration, urine, biopsy, coelomic fluid, or coelome lavage fluid.

6. The method as set forth in claim 3, wherein the cancer is rectal cancer, colonic cancer, gastric cancer, esophagus cancer, lung cancer, mammary cancer, liver cancer, biliary tract cancer, pancreas cancer, thyroid cancer, bladder cancer, prostate cancer, scrotal cancer, cervix cancer, cancer of uterine body, cervical cancer, or ovarian cancer.

* * * * *

SEQUENCE LISTING

```
<160> NUMBER OF SEQ ID NOS: 34

<210> SEQ ID NO 1
<211> LENGTH: 2109
<212> TYPE: DNA
<213> ORGANISM: Homo sapiens

<400> SEQUENCE: 1
atggagtctc cctcggcccc tccccacaga tggtgcatcc cctggcagag gctcctgctc      60
acagcctcac ttctaacctt ctggaacccg cccaccactg ccaagctcac tattgaatcc     120
acgccgttca atgtcgcaga ggggaaggag gtgcttctac ttgtccacaa tctgccccag     180 catcttttg gctacagctg gtacaaaggt gaaagagtgg atggcaaccg tcaaattata      240
ggatatgtaa taggaactca acaagctacc ccagggcccg catacagtgg tcgagagata     300 atataccca atgcatccct gctgatccag aacatcatcc agaatgacac aggattctac      360
accctacacg tcataaagtc agatcttgtg aatgaagaag caactggcca gttccgggta     420
tacccggagc tgcccaagcc ctccatctcc agcaacaact ccaaacccgt ggaggacaag     480
gatgctgtgg ccttcacctg tgaacctgag actcaggacg caacctacct gtggtgggta     540
aacaatcaga gcctcccggt cagtccagg ctgcagctgt ccaatggcaa caggaccctc     600
actctattca atgtcacaag aaatgacaca gcaagctaca atgtgaaac ccagaaccca      660 gtgagtgcca ggcgcagtga ttcagtcatc ctgaatgtcc tctatggccc ggatgccccc     720
accatttccc ctctaaacac atcttacaga tcaggggaaa atctgaacct ctcctgccac     780
gcagcctcta acccacctgc acagtactct tggtttgtca atgggacttt ccagcaatcc     840
acccaagagc tctttatccc caacatcact gtgaataata gtggatccta tacgtgccaa     900
gcccataact cagacactgg cctcaatagg accacagtca cgacgatcac agtctatgca     960
gagccaccca acccttcat caccagcaac aactccaacc ccgtggagga tgaggatgct    1020
gtagccttaa cctgtgaacc tgagattcag aacacaacct acctgtggtg ggtaaataat    1080
```

-continued

```
cagagcctcc cggtcagtcc caggctgcag ctgtccaatg acaacaggac cctcactcta   1140
ctcagtgtca caaggaatga tgtaggaccc tatgagtgtg gaatccagaa cgaattaagt   1200
gttgaccaca gcgacccagt catcctgaat gtcctctatg cccagacga ccccaccatt    1260 tcccctcat acacctatta ccgtccaggg gtgaacctca gcctctcctg ccatgcagcc    1320
tctaacccac ctgcacagta ttcttggctg attgatggga acatccagca acacacacaa   1380
gagctcttta tctccaacat cactgagaag aacagcggac tctatacctg ccaggccaat   1440
aactcagcca gtggccacag caggactaca gtcaagacaa tcacagtctc tgcggagctg   1500
cccaagccct ccatctccag caacaactcc aaacccgtgg aggacaagga tgctgtggcc   1560
ttcacctgtg aacctgaggc tcagaacaca acctacctgt ggtgggtaaa tggtcagagc   1620
ctcccagtca gtcccaggct gcagctgtcc aatggcaaca ggaccctcac tctattcaat   1680
gtcacaagaa atgacgcaag agcctatgta tgtggaatcc agaactcagt gagtgcaaac   1740
cgcagtgacc cagtcaccct ggatgtcctc tatgggccgg acaccccat catttccccc    1800 ccagactcgt cttacctttc gggagcgaac ctcaacctct cctgccactc ggcctctaac   1860
ccatccccgc agtattcttg gcgtatcaat gggataccgc agcaacacac acaagttctc   1920
tttatcgcca aaatcacgcc aaataataac gggacctatg cctgttttgt ctctaacttg   1980
gctactggcc gcaataattc catagtcaag agcatcacag tctctgcatc tggaacttct   2040
cctggtctct cagctggggc cactgtcggc atcatgattg gagtgctggt tggggttgct   2100
ctgatatag                                                           2109
```

<210> SEQ ID NO 2
<211> LENGTH: 21
<212> TYPE: DNA
<213> ORGANISM: Homo sapiens
<220> FEATURE:
<221> NAME/KEY: misc_feature
<223> OTHER INFORMATION: region complementary to 881-901 of SEQ ID NO:1

<400> SEQUENCE: 2

```
cttggcacgt ataggatcca c                                              21
```

<210> SEQ ID NO 3
<211> LENGTH: 18
<212> TYPE: DNA
<213> ORGANISM: Homo sapiens
<220> FEATURE:
<221> NAME/KEY: misc_feature
<223> OTHER INFORMATION: region complementary to 881-898 of SEQ ID NO:1

<400> SEQUENCE: 3

```
ggcacgtata ggatccac                                                  18
```

<210> SEQ ID NO 4
<211> LENGTH: 19
<212> TYPE: DNA
<213> ORGANISM: Homo sapiens
<220> FEATURE:
<221> NAME/KEY: misc_feature
<223> OTHER INFORMATION: region complementary to 881-899 of SEQ ID NO:1

<400> SEQUENCE: 4

```
tggcacgtat aggatccac                                                 19
```

<210> SEQ ID NO 5
<211> LENGTH: 19
<212> TYPE: DNA

```
<213> ORGANISM: Homo sapiens
<220> FEATURE:
<221> NAME/KEY: misc_feature
<223> OTHER INFORMATION: region of 830-848 of SEQ ID NO:1

<400> SEQUENCE: 5
tccagcaatc cacccaaga                                                    19

<210> SEQ ID NO 6
<211> LENGTH: 20
<212> TYPE: DNA
<213> ORGANISM: Homo sapiens
<220> FEATURE:
<221> NAME/KEY: misc_feature
<223> OTHER INFORMATION: region of 830-849 of SEQ ID NO:1

<400> SEQUENCE: 6
tccagcaatc cacccaagag                                                   20

<210> SEQ ID NO 7
<211> LENGTH: 21
<212> TYPE: DNA
<213> ORGANISM: Homo sapiens
<220> FEATURE:
<221> NAME/KEY: misc_feature
<223> OTHER INFORMATION: region of 911-931 of SEQ ID NO:1

<400> SEQUENCE: 7
cagacactgg cctcaatagg a                                                 21

<210> SEQ ID NO 8
<211> LENGTH: 19
<212> TYPE: DNA
<213> ORGANISM: Homo sapiens
<220> FEATURE:
<221> NAME/KEY: misc_feature
<223> OTHER INFORMATION: region of 913-931 of SEQ ID NO:1

<400> SEQUENCE: 8
gacactggcc tcaatagga                                                    19

<210> SEQ ID NO 9
<211> LENGTH: 19
<212> TYPE: DNA
<213> ORGANISM: Homo sapiens
<220> FEATURE:
<221> NAME/KEY: misc_feature
<223> OTHER INFORMATION: region complementary to 956-974 of SEQ ID NO:1

<400> SEQUENCE: 9
ggtttgggtg gctctgcat                                                    19

<210> SEQ ID NO 10
<211> LENGTH: 19
<212> TYPE: DNA
<213> ORGANISM: Homo sapiens
<220> FEATURE:
<221> NAME/KEY: misc_feature
<223> OTHER INFORMATION: region complementary to 954-972 of SEQ ID NO:1

<400> SEQUENCE: 10
tttgggtggc tctgcatag                                                    19

<210> SEQ ID NO 11
<211> LENGTH: 17
<212> TYPE: DNA
<213> ORGANISM: Homo sapiens
```

```
<220> FEATURE:
<221> NAME/KEY: misc_feature
<223> OTHER INFORMATION: region complementary to 958-974 of SEQ ID NO:1

<400> SEQUENCE: 11
ggtttgggtg gctctgc                                                    17

<210> SEQ ID NO 12
<211> LENGTH: 18
<212> TYPE: DNA
<213> ORGANISM: Homo sapiens
<220> FEATURE:
<221> NAME/KEY: misc_feature
<223> OTHER INFORMATION: region complementary to 957-974 of SEQ ID NO:1

<400> SEQUENCE: 12
ggtttgggtg gctctgca                                                   18

<210> SEQ ID NO 13
<211> LENGTH: 20
<212> TYPE: DNA
<213> ORGANISM: Artificial Sequence
<220> FEATURE:
<223> OTHER INFORMATION: chemically-synthesized nucleic acid
      amplification primer

<400> SEQUENCE: 13
tgcacagtac tcttggtttg                                                 20

<210> SEQ ID NO 14
<211> LENGTH: 40
<212> TYPE: DNA
<213> ORGANISM: Artificial Sequence
<220> FEATURE:
<223> OTHER INFORMATION: chemically-synthesized nucleic acid
      amplification primer

<400> SEQUENCE: 14
cttggcacgt ataggatcca ctccagcaat ccacccaaga                           40

<210> SEQ ID NO 15
<211> LENGTH: 37
<212> TYPE: DNA
<213> ORGANISM: Artificial Sequence
<220> FEATURE:
<223> OTHER INFORMATION: chemically-synthesized nucleic acid
      amplification primer

<400> SEQUENCE: 15
ggcacgtata ggatccactc cagcaatcca cccaaga                              37

<210> SEQ ID NO 16
<211> LENGTH: 38
<212> TYPE: DNA
<213> ORGANISM: Artificial Sequence
<220> FEATURE:
<223> OTHER INFORMATION: chemically-synthesized nucleic acid
      amplification primer

<400> SEQUENCE: 16
tggcacgtat aggatccact ccagcaatcc acccaaga                             38

<210> SEQ ID NO 17
<211> LENGTH: 41
<212> TYPE: DNA
<213> ORGANISM: Artificial Sequence
<220> FEATURE:
```

<223> OTHER INFORMATION: chemically-synthesized nucleic acid
      amplification primer

<400> SEQUENCE: 17
cttggcacgt ataggatcca ctccagcaat ccacccaaga g                          41

<210> SEQ ID NO 18
<211> LENGTH: 40
<212> TYPE: DNA
<213> ORGANISM: Artificial Sequence
<220> FEATURE:
<223> OTHER INFORMATION: chemically-synthesized nucleic acid
      amplification primer

<400> SEQUENCE: 18
cagacactgg cctcaatagg aggtttgggt ggctctgcat                            40

<210> SEQ ID NO 19
<211> LENGTH: 40
<212> TYPE: DNA
<213> ORGANISM: Artificial Sequence
<220> FEATURE:
<223> OTHER INFORMATION: chemically-synthesized nucleic acid
      amplification primer

<400> SEQUENCE: 19
cagacactgg cctcaatagg atttgggtgg ctctgcatag                            40

<210> SEQ ID NO 20
<211> LENGTH: 38
<212> TYPE: DNA
<213> ORGANISM: Artificial Sequence
<220> FEATURE:
<223> OTHER INFORMATION: chemically-synthesized nucleic acid
      amplification primer

<400> SEQUENCE: 20
cagacactgg cctcaatagg aggtttgggt ggctctgc                              38

<210> SEQ ID NO 21
<211> LENGTH: 38
<212> TYPE: DNA
<213> ORGANISM: Artificial Sequence
<220> FEATURE:
<223> OTHER INFORMATION: chemically-synthesized nucleic acid
      amplification primer

<400> SEQUENCE: 21
gacactggcc tcaataggag gtttgggtgg ctctgcat                              38

<210> SEQ ID NO 22
<211> LENGTH: 39
<212> TYPE: DNA
<213> ORGANISM: Artificial Sequence
<220> FEATURE:
<223> OTHER INFORMATION: chemically-synthesized nucleic acid
      amplification primer

<400> SEQUENCE: 22
cagacactgg cctcaatagg aggtttgggt ggctctgca                             39

<210> SEQ ID NO 23
<211> LENGTH: 19
<212> TYPE: DNA
<213> ORGANISM: Artificial Sequence
<220> FEATURE:
<223> OTHER INFORMATION: chemically-synthesized nucleic acid -continued

```
amplification primer

<400> SEQUENCE: 23
tcacagtgat gttggggat                                                19

<210> SEQ ID NO 24
<211> LENGTH: 18
<212> TYPE: DNA
<213> ORGANISM: Artificial Sequence
<220> FEATURE:
<223> OTHER INFORMATION: chemically-synthesized nucleic acid
      amplification primer

<400> SEQUENCE: 24
acagtcacga cgatcaca                                                 18

<210> SEQ ID NO 25
<211> LENGTH: 19
<212> TYPE: DNA
<213> ORGANISM: Artificial Sequence
<220> FEATURE:
<223> OTHER INFORMATION: chemically-synthesized nucleic acid
      amplification primer

<400> SEQUENCE: 25
cacagtcacg acgatcaca                                                19

<210> SEQ ID NO 26
<211> LENGTH: 19
<212> TYPE: DNA
<213> ORGANISM: Artificial Sequence
<220> FEATURE:
<223> OTHER INFORMATION: chemically-synthesized nucleic acid
      amplification primer

<400> SEQUENCE: 26
acagtcacga cgatcacag                                                19

<210> SEQ ID NO 27
<211> LENGTH: 38
<212> TYPE: DNA
<213> ORGANISM: Artificial Sequence
<220> FEATURE:
<223> OTHER INFORMATION: chemically-synthesized nucleic acid
      amplification primer

<400> SEQUENCE: 27
taggtcccgt tattatttgg cccatccccg cagtattc                           38

<210> SEQ ID NO 28
<211> LENGTH: 42
<212> TYPE: DNA
<213> ORGANISM: Artificial Sequence
<220> FEATURE:
<223> OTHER INFORMATION: chemically-synthesized nucleic acid
      amplification primer

<400> SEQUENCE: 28
tttgtctcta acttggctac tggggagaag ttccagatgc ag                      42

<210> SEQ ID NO 29
<211> LENGTH: 17
<212> TYPE: DNA
<213> ORGANISM: Artificial Sequence
<220> FEATURE:
<223> OTHER INFORMATION: chemically-synthesized nucleic acid
      amplification primer
```

```
<400> SEQUENCE: 29
tcttaccttt cgggagc                                                      17

<210> SEQ ID NO 30
<211> LENGTH: 18
<212> TYPE: DNA
<213> ORGANISM: Artificial Sequence
<220> FEATURE:
<223> OTHER INFORMATION: chemically-synthesized nucleic acid
      amplification primer

<400> SEQUENCE: 30
ccaaccagca ctccaatc                                                     18

<210> SEQ ID NO 31
<211> LENGTH: 19
<212> TYPE: DNA
<213> ORGANISM: Artificial Sequence
<220> FEATURE:
<223> OTHER INFORMATION: chemically-synthesized nucleic acid
      amplification primer

<400> SEQUENCE: 31
gcggtatccc attgatacg                                                    19

<210> SEQ ID NO 32
<211> LENGTH: 24
<212> TYPE: DNA
<213> ORGANISM: Artificial Sequence
<220> FEATURE:
<223> OTHER INFORMATION: chemically-synthesized nucleic acid
      amplification primer

<400> SEQUENCE: 32
cgcaataatt ccatagtcaa gagc                                              24

<210> SEQ ID NO 33
<211> LENGTH: 21
<212> TYPE: DNA
<213> ORGANISM: Artificial Sequence
<220> FEATURE:
<223> OTHER INFORMATION: chemically-synthesized nucleic acid
      amplification primer

<400> SEQUENCE: 33
cggaattcat ggagtctccc t                                                 21

<210> SEQ ID NO 34
<211> LENGTH: 22
<212> TYPE: DNA
<213> ORGANISM: Artificial Sequence
<220> FEATURE:
<223> OTHER INFORMATION: chemically-synthesized nucleic acid
      amplification primer

<400> SEQUENCE: 34
cgtctagact atatcagagc aa                                                22
```